US009113835B2

(12) United States Patent
Li

(10) Patent No.: US 9,113,835 B2
(45) Date of Patent: Aug. 25, 2015

(54) SYSTEM AND METHOD FOR GENERATING A RENDERING OF A VOLUME OF TISSUE BASED UPON DIFFERENTIAL TIME-OF-FLIGHT DATA

(75) Inventor: Cuiping Li, Troy, MI (US)

(73) Assignee: Delphinus Medical Technologies, Inc., Plymouth, MI (US)

( * ) Notice: Subject to any disclaimer, the term of this patent is extended or adjusted under 35 U.S.C. 154(b) by 762 days.

(21) Appl. No.: 13/368,169

(22) Filed: Feb. 7, 2012

(65) Prior Publication Data
US 2012/0283566 A1    Nov. 8, 2012

Related U.S. Application Data

(60) Provisional application No. 61/440,530, filed on Feb. 8, 2011.

(51) Int. Cl.
*A61B 8/15*   (2006.01)
*G06T 7/00*   (2006.01)
*A61B 8/08*   (2006.01)
*A61B 8/00*   (2006.01)

(52) U.S. Cl.
CPC ............... *A61B 8/15* (2013.01); *A61B 8/0825* (2013.01); *A61B 8/4494* (2013.01); *A61B 8/5207* (2013.01); *G06T 7/0012* (2013.01); *G06T 7/0026* (2013.01); *G06T 7/0032* (2013.01); *A61B 8/406* (2013.01); *A61B 8/4444* (2013.01); *A61B 8/4483* (2013.01); *A61B 8/587* (2013.01)

(58) Field of Classification Search
CPC ...... A61B 8/15; A61B 8/4494; A61B 8/5207; A61B 8/0825; A61B 8/587; A61B 8/406; G06T 7/0012; G06T 7/0026; G06T 7/0032
See application file for complete search history.

(56) References Cited

U.S. PATENT DOCUMENTS 3,771,355 A * 11/1973 Sachs .............................. 73/597
4,431,008 A *  2/1984 Wanner et al. ................ 600/438
4,733,562 A    3/1988 Saugeon
(Continued)

OTHER PUBLICATIONS

Chan et al., An Agglomeration Multigrid Method for Unstructured Grids, Contemporary Mathematics, vol. 218, 1998.
(Continued)

*Primary Examiner* — Amanda Lauritzen Moher
(74) *Attorney, Agent, or Firm* — Jeffrey Schox; Ivan Wong

(57) ABSTRACT

The system of one embodiment for imaging tissue includes ultrasound emitters configured to surround and emit acoustic waveforms toward the tissue, ultrasound receivers configured to surround and receive acoustic waveforms scattered by the tissue, and a processor configured for determining an observed differential time-of-flight (ToF) dataset and generating an acoustic speed rendering of the tissue based on the observed differential ToF dataset. The method of one embodiment for imaging tissue includes receiving data representative of acoustic waveforms scattered by the tissue, determining an observed differential ToF dataset, performing forward modeling to generate a calculated differential ToF dataset based on an acoustic speed model, performing inverse modeling to generate an acoustic speed model based on the observed and calculated differential ToF datasets, iteratively repeating forward modeling and inverse modeling until convergence is met with a final acoustic speed model, and generating an acoustic speed rendering from the final acoustic speed model.

19 Claims, 6 Drawing Sheets

(56) References Cited

U.S. PATENT DOCUMENTS 5,296,910 A 3/1994 Cole
2005/0196025 A1 9/2005 Schofield

OTHER PUBLICATIONS

McCormick et al., Multigrid solution of a linearized, regularized least-squares problem in electrical impedance tomography, Inverse Problems 9, 1993, 697-713.

Oh et al., Multigrid Tomographic Inversion With Variable Resolution Data and Image Spaces, IEEE Transactions on Image Proessing, vol. 15, No. 9, Sep. 2006.

Quan et al., Sound-speed tomography using first-arrival transmission ultrasound for a ring array, Medical Imaging 2007: Ultrasonic Imaging and Signal Processing, Proc. of SPIE vol. 6513.

Zhang et al., A comparison of material classification techniques for ultrasound inverse imaging, J. Acoust. Soc. Am. 111 (1), Pt. 1, Jan. 2002.

\* cited by examiner

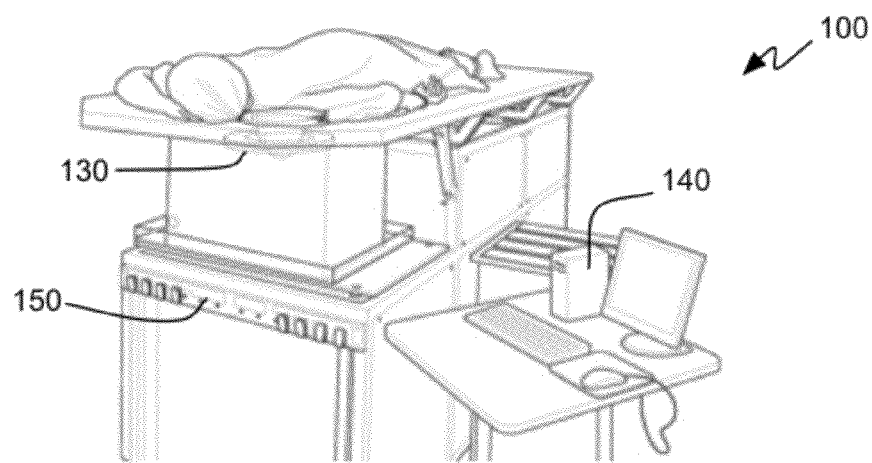
FIGURE 1A
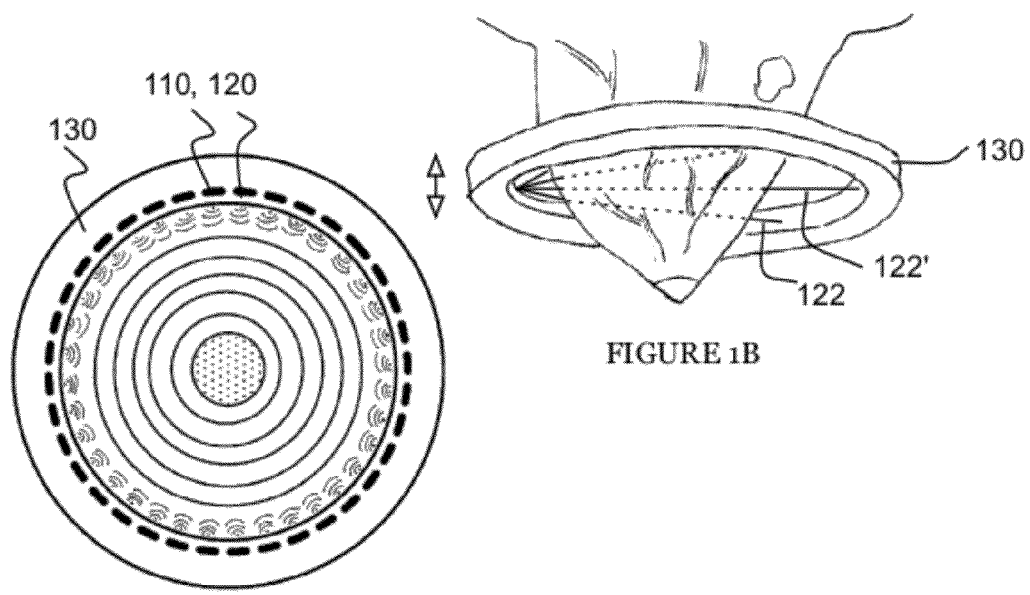
FIGURE 1B
FIGURE 1C (a) Sound speed reconstruction with DD tomography  (b) Sound speed reconstruction with standard tomography  (c) X-ray CT scan

| Material number | Known sound speed ($m/s$) | DD tomography ($m/s$) | Standard tomography ($m/s$) |
|---|---|---|---|
| 1 | 1549 | 1546 | 1534 |
| 2 | 1559 | 1535 | 1524 |
| 3 | 1470 | 1471 | 1464 |
| 4 | 1470 | 1500 | 1495 |
| 5 | 1515 | 1516 | 1507 |
| 6 | 1470 | 1475 | 1470 |

(a) Gelatin phantom  (b) Sound speed reconstruction with DD tomography  (c) Sound speed reconstruction standard tomography (a) Sound speed reconstruction with DD tomography  (b) Sound speed reconstruction with standard tomography  (c) Reflection image

SYSTEM AND METHOD FOR GENERATING A RENDERING OF A VOLUME OF TISSUE BASED UPON DIFFERENTIAL TIME-OF-FLIGHT DATA

CROSS-REFERENCE TO RELATED APPLICATIONS

This application claims the benefit of U.S. Provisional Patent Application Ser. No. 61/440,530, entitled "Method for Imaging a Volume of Tissue with Double Difference Tomography" and filed 8 Feb. 2011, the entirety of which is incorporated herein by this reference.

TECHNICAL FIELD

This invention relates generally to the medical imaging field, and more specifically to an improved system and method for imaging a volume of tissue.

BACKGROUND

Early detection of breast cancer and other types of cancer is typically an important factor to successfully treat cancer. Ultrasound tomography is a promising imaging modality that has the potential to improve medical imaging of tissue for screening and diagnosis purposes compared to conventional imaging techniques. For instance, mammography is the current standard tool for breast screening, but involves ionizing radiation that precludes frequent imaging, plus mammography has a low sensitivity for detection of cancer in patients with dense breast tissue, which leads to a relatively high false negative rate. As another example, magnetic resonance imaging (MRI) is prohibitively expensive for routine and also has limited accessibility.

However, the quality of ultrasound ray tomography relies largely on the accuracy of the picked absolute time-of-flights, or the measured overall time it takes for an acoustic wave to travel between an ultrasound emitter-receiver pair. Furthermore, standard ultrasound ray tomography depends heavily on accurate and clear onset of signal arrivals, but typically contain systematic errors or other sources of uncertainty. Current ultrasound ray tomography methods may use the time-of-flight acoustic data to create an acoustic speed reconstructions, but inaccuracy of picked time-of-flights downgrades the quality of the resulting images (for example, the resulting reconstructions may not capture particular distinct characteristics of the tissue), which has the potential to greatly affect screening and diagnosis conclusions. Thus, there is a need in the medical imaging field to create an improved system and method for imaging a volume of tissue. This invention provides such an improved system and method for imaging a volume of tissue.

BRIEF DESCRIPTION OF THE FIGURES

FIGS. 1A-1C are schematics of the system, a perspective schematic view of a transducer ring, and a top schematic view of the transducer ring, respectively, of a preferred embodiment;

DESCRIPTION OF THE PREFERRED EMBODIMENTS

The following description of preferred embodiments of the invention is not intended to limit the invention to these preferred embodiments, but rather to enable any person skilled in the art to make and use this invention.

System for Imaging a Volume of Tissue

Figure 2:
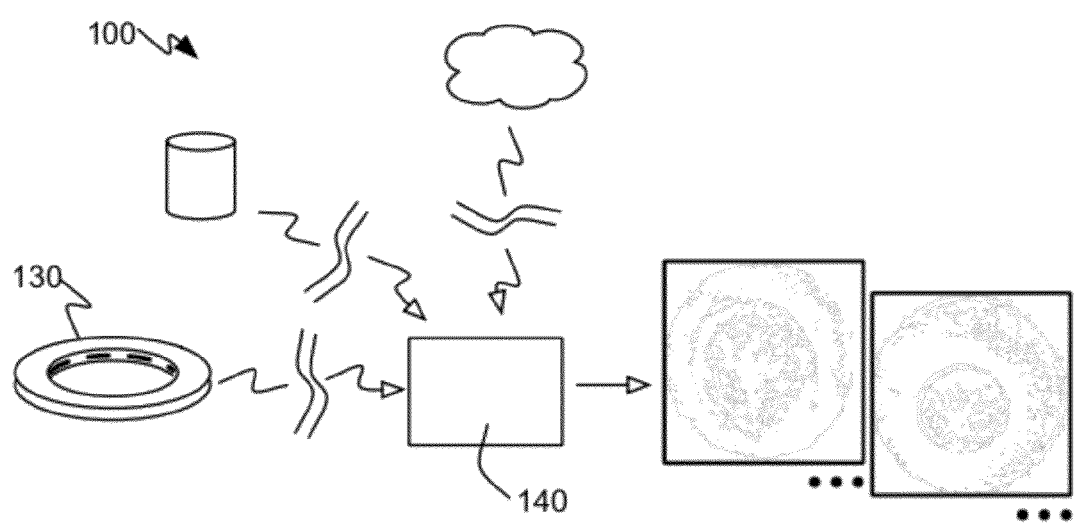
FIG. 2 is a schematic of the processor of the system of a preferred embodiment.

As shown in FIGS. 1-2, the system 100 of a preferred embodiment for imaging a volume of tissue includes: an array of ultrasound emitters no configured to surround the volume of tissue and emit acoustic waveforms toward the volume of tissue; an array of ultrasound receivers 120 configured to surround the volume of tissue and to receive acoustic waveforms scattered by the volume of tissue, each acoustic waveform corresponding to a respective emitter-receiver pair; and a processor 140 configured for determining an observed differential time-of-flight data set based on relative observed time-of-flights of adjacent scattered acoustic waveforms corresponding to adjacent emitter-receiver pairs, determining a calculated differential time-of-flight data set; and generating an acoustic speed rendering of the volume of tissue at least partially based on the observed differential time-of-flight data set. In generating an acoustic speed rendering of the volume of tissue, the processor 140 is preferably configured to calculate the "double difference," or the difference between observed (measured) and calculated (based on a generated acoustic speed model of the volume of tissue) differential time-of-flights (ToFs) for two physically adjacent waveforms, which may be expressed as $\Delta t_i - \Delta t_k = (t_i^{obs} - t_k^{obs}) - (t_i^{cal} - t_k^{cal})$ mathematically. The processes performed by the preferred processor are described in further detail below. The system 100 is preferably used to image a volume of tissue, such as breast tissue, for screening and/or diagnosis of cancer within the volume of tissue. In other applications, the system can be used to characterize regions of interest in the tissue (e.g., to characterize suspicious masses as a tumor, a fibroadenoma, a cyst, another benign mass, or any suitable classification) or for monitoring status of the tissue such as during a cancer treatment. However, the system can be used in any suitable application for imaging any suitable kind of tissue with ultrasound tomography.

The preferred system 100 for imaging a volume of tissue uses accurate differential ToF data and results in an acoustic speed rendering of the tissue that is more precise and has better resolution than those available through standard ultrasound ray tomography methods, which utilize absolute ToF between a single emitter-receiver pair. Furthermore, the preferred system 100 employs double difference tomography, through which known systematic data acquisition delays and other systematic errors are canceled out and therefore do not affect the final acoustic speed images of the volume of tissue. The accuracy of double difference tomography mainly relies on relative time shift between waveforms that can be accurately estimated using cross-correlation for waveforms with similar shape. In contrast, the accuracy of standard ray tomography depends heavily on clear onset time of signal arrivals and precise estimation of system delays during data acquisition, both of which are more prone to errors than waveform cross-correlation.

As shown in FIG. 1C, the preferred system 100 can include an array of ultrasound emitters 110 and ultrasound receivers 120. The array of ultrasound emitters 110 preferably functions to irradiate the volume of tissue with acoustic waveforms from multiple locations distributed around the volume of tissue. The array of ultrasound receivers 120 preferably functions to receive the acoustic waveforms, a portion of which are preferably scattered by the volume of tissue. In a preferred embodiment, as shown in FIG. 1C, the arrays of ultrasound emitters 110 and receivers 120 surround the tissue such that each ultrasound emitter 110 is flanked by and is adjacent to at least two other ultrasound emitters, and/or each ultrasound receiver 120 is flanked by and is adjacent to at least two other ultrasound receivers. In other words, the ultrasound emitters no and the ultrasound receivers 120 are preferably arranged in a substantially continuous and/or contiguous manner surrounding the tissue. By irradiating adjacent common emitter waveforms from locations collectively surrounding the tissue, the ultrasound emitters 110 provide data coverage that is more homogeneous and denser than standard ultrasound systems having linear ultrasound emitter arrays. Furthermore, by receiving adjacent common receiver waveforms, the ultrasound receivers 120 provide increased accuracy of cross-correlation of physically adjacent waveforms, thereby resulting in a higher-quality acoustic speed rendering of the volume of tissue.

In particular, the ultrasound emitters 110 and ultrasound receivers 120 are preferably arranged in an axially symmetrical arrangement. More preferably, in an exemplary embodiment shown in FIGS. 1A-1C, the system 100 includes a scanning apparatus including a ring-shaped transducer 130 that includes tissue-encircling arrays of ultrasound emitters 110 and receivers 120 for scanning breast tissue of a patient. As shown in FIG. 1A, during a scan, the patient positions herself or himself facedown on a flexible bed having a hole in a chest region of the bed. As shown in FIG. 1B, the breast tissue of the patient passes through the hole in the bed and is positioned such that the transducer 130 surrounds the tissue. The transducer 130 can preferably be immersed in a tank of water or another suitable acoustic coupling medium, and can be fixed to a gantry that moves the transducer 130 in a path to pass along the tissue in an anterior-posterior direction, thereby preferably imaging the entire breast (or alternatively a selected portion of the breast or other suitable tissue).

As shown in FIG. 1A, the preferred system 100 can further include a controller 150 that controls the transducer 130 and its ultrasound emitters and receivers 110, 120 (e.g., speed of transducer movement, activation of ultrasound emitters and/or receivers). In one specific variation of the preferred system 100, the ring transducer 130 includes 256 evenly distributed ultrasound elements that each emits a fan beam of ultrasound signals towards the breast tissue and opposite end of the ring, and receives ultrasound signals scattered by the breast tissue (e.g., transmitted by and/or reflected by the tissue) during scanning of the tissue. In one example, the transmitted broadband ultrasound signals have a central frequency around 2 MHz and the received ultrasound signals are recorded at a sampling rate of 8.33 MHz. However, the ring transducer may have any suitable number of elements that emit and record ultrasound signals at any suitable frequencies. Furthermore, in alternative embodiments, scanning may be performed with any suitable transducer having arrays of ultrasound emitters and ultrasound receivers surrounding the volume of the tissue.

As shown in FIG. 1A, FIG. 1B, and FIG. 2, the preferred system 100 can further include a processor 140. The processor 140 preferably functions to generate an acoustic speed rendering or image of the volume of tissue based on the received acoustic waveforms. In particular, the processor 140 is preferably configured to determine an observed differential time-of-flight data set based on the received acoustic waveforms, determine a calculated differential time-of-flight data set based on an acoustic speed model, and generate an acoustic speed rendering incorporating a "double difference" term for physically adjacent waveforms, or the difference between observed (measured) and calculated (based on a generated acoustic speed model) differential ToFs for the physically adjacent waveforms. The "double difference" term for two adjacent waveforms i and k (represented as 122 and 122' in FIG. 1B) may be expressed as $\Delta t_i - \Delta t_k = (t_i^{obs} - t_k^{obs}) - (t_i^{cal} - t_k^{cal})$ mathematically. The processor 140 is preferably configured to perform the method further described below. The processor 140 can be coupled directly to the scanning apparatus (e.g., part of a local workstation in direct communication to the ultrasound emitters and receivers), and/or can be communicatively coupled to a storage device (e.g., a server or other computer-readable storage medium) to receive data representative of the received acoustic waveforms.

As shown in FIG. 2, the preferred processor 140 can be configured to produce one or more two-dimensional image slices of the tissue under examination. Preferably, the acoustic speed rendering can include two-dimensional "slices" of the tissue corresponding to respective cross-sections of the volume of tissue (e.g., image slices of discrete anterior-posterior positions of breast tissue), and/or a three-dimensional rendering resulting from a composite of multiple two-dimensional cross-sectional images, or alternatively resulting from scanning the volume of tissue in a three-dimensional manner. In some applications, the acoustic speed rendering can be combined and/or compared with additional renderings of the volume of tissue (e.g., attenuation, reflection).

Method for Imaging a Volume of Tissue

Figure 3:
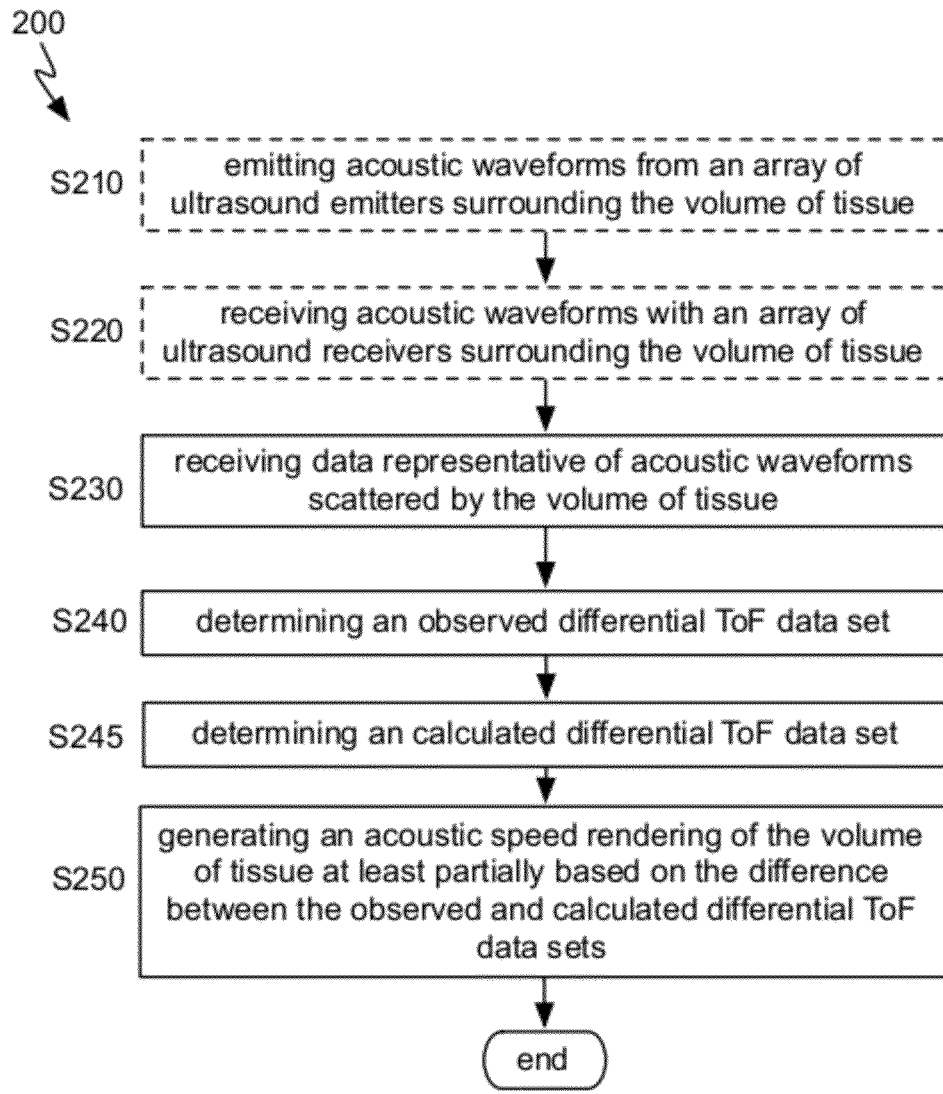
FIGS. 3-6 are flowcharts depicting a method of a preferred embodiment and variations thereof.

As shown in FIG. 3, the method of a preferred embodiment for imaging a volume of tissue includes: in block S230, receiving data representative of acoustic waveforms scattered by the volume of tissue; in block S240, determining an observed differential time-of-flight data set; in block S245, determining a calculated differential time-of-flight data set; and in block S250, generating an acoustic speed rendering of the volume of tissue at least partially based on the observed differential time-of-flight data set. Generating an acoustic speed rendering preferably incorporates a "double difference" term, or the difference between observed (measured) and calculated (based on a generated acoustic speed model) differential time-of-flights (ToFs) for adjacent waveforms i and k, which may be expressed as $\Delta t_i - \Delta t_k = (t_i^{obs} - t_k^{obs}) - (t_i^{cal} - t_k^{cal})$ mathematically. In some embodiments, the preferred method further includes in block S210 emitting acoustic waveforms from an array of ultrasound emitters surrounding the volume of tissue, and in block S220 receiving acoustic waveforms with an array of ultrasound receivers surrounding the volume of tissue. The preferred method functions to image a volume of tissue with increased precision, image resolution, and accuracy. In particular, the preferred method may be used to image breast tissue, for screening and/or diagnosis of cancer within the tissue. In other applications, the preferred method may be used to characterize regions of interest in the tissue (e.g., to characterize suspicious masses as a tumor, a fibroadenoma, a cyst, another benign mass, or any suitable classification) or for monitoring status of the tissue such as during a cancer treatment. However, the preferred method and/or any variations thereof can be used in any suitable application for imaging any suitable kind of tissue with ultrasound tomography.

As shown in FIG. 3, block S210 recites emitting acoustic waveforms from an array of ultrasound emitters surrounding the volume of tissue, and block S220 recites receiving acoustic waveforms with an array of ultrasound receivers surrounding the volume of tissue. Blocks S210 and S220 preferably function to scan and gather ultrasound data regarding the volume of tissue. Block S210 is preferably performed with an array of ultrasound emitters in which each ultrasound emitter is flanked by, and more preferably contiguous and/or continually disposed with, at least two other ultrasound emitters and/or receivers in a circular ring or other suitable axially symmetrical transducer configured to receive and surround the volume of tissue. Similarly, block S220 is preferably performed with an array of ultrasound receivers in which each ultrasound receiver is flanked by, and more preferably contiguous with, at least two other ultrasound receivers and/or emitters in a circular ring or other suitable axially symmetrical transducer configured to receive and surround the volume of tissue. In a preferred embodiment, blocks S210 and S220 are performed with a ring transducer in a system as described above, but may alternatively be performed with any suitable transducer. The method may further include recording data representative of the received acoustic waveforms, such as by storing acquired imaging data in a computer-readable storage medium.

As shown in FIG. 3, block S230 recites receiving data representative of acoustic waveforms scattered by the volume of tissue. In a preferred embodiment, block S230 includes receiving data directly from a transducer. In alternative variations, block S230 includes receiving data from a computer-readable medium or storage, such as a server, cloud storage, hard drive, flash memory, optical device (CD or DVD), or other suitable device capable of receiving, storing, and/or otherwise transferring data.

Figure 4:
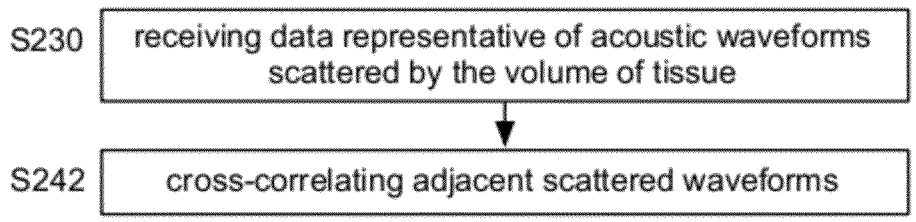

As shown in FIG. 3, block S240 recites determining an observed differential time-of-flight data set. Block S240 preferably functions to characterize the similarities or differences between sets of physically adjacent, received acoustic waveforms as a function of time lag. As shown in FIG. 4, the preferred method can additionally include block S242, which recites cross-correlating adjacent scattered waveforms. Alternatively, the method can include manual picking or any suitable process for determining the observed differential ToF data set. Preferably, the axial symmetry of the transducer arrangement of ultrasound emitters and receivers inherently allows physically adjacent acoustic waveforms to be similar, and the resulting data continuity around the transducer enables highly accurate cross-correlation calculations, thereby promoting more accurate calculation of observed differential ToF data. Because any systematic errors (such as systematic data acquisition delays) appear similarly for physically adjacent waveforms, block S242 preferably cancels these systematic errors such that these errors have no effect on the final acoustic speed images. Block S242 is preferably performed on a group of physically adjacent waveforms from both common transmitter gather (that is, from a common general source location) and common receiver gather (that is, from a common general receiver location). Block S242 is preferably performed for a portion of all waveforms received, and repeated for multiple portions of all recorded waveforms (the multiple complementary subsets of the recorded waveforms may be cross-correlated). For example, block S242 can include cross-correlating eighteen adjacent waveforms having both common transmitter gather and common receiver gather.

Figure 5:
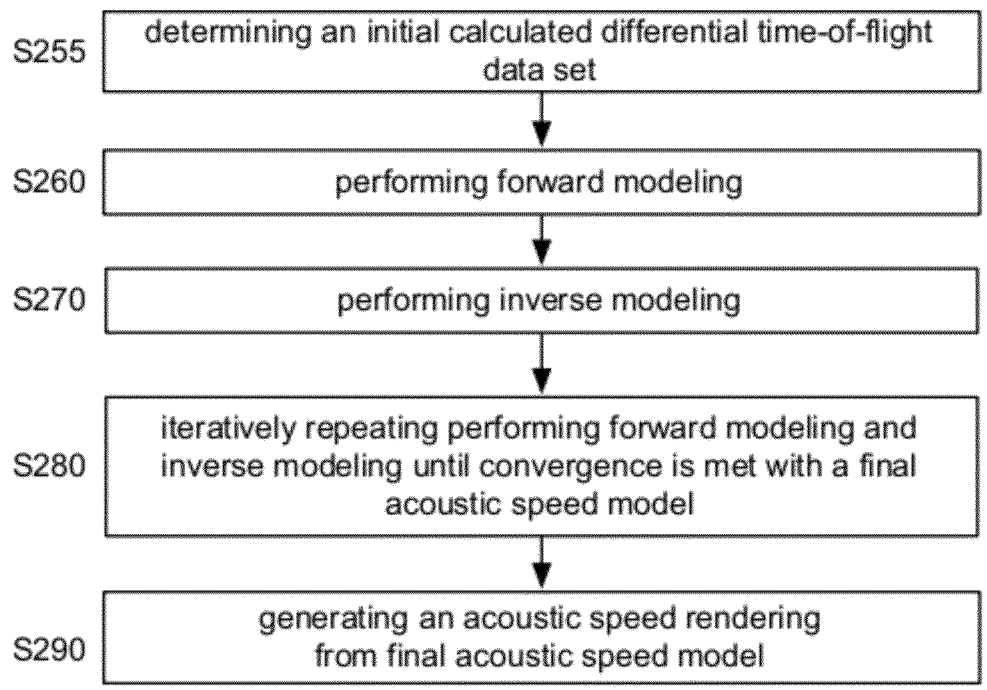

As shown in FIG. 3, block S245 recites determining a calculated differential time-of-flight data set. The calculated differential time-of-flight data set is preferably based on an acoustic model. Block S245 preferably functions to determine a quantity that, when compared to the observed differential time-of-flight data set, provides a measure of accuracy of an acoustic speed model relative to the volume of tissue. As shown in FIG. 5, a variation of the method includes block S255, which recites determining an initial calculated differential time-of-flight data set. Block S255 preferably functions to determine at least an initial calculated differential ToF data set based on an initial (given) acoustic speed model. The initial acoustic speed model may be homogeneous (uniform acoustic speed throughout the model of the tissue and/or scan region) or inhomogeneous, or any suitable acoustic speed model. In some embodiments, the initial acoustic speed model may be based empirically through known acoustic speeds of at least one feature of the volume of tissue (e.g., known average acoustic speed of fatty tissue), prior scans of the same or similar volume of tissue, and/or any suitable factors. In some embodiments, the method may alternatively include receiving an initial calculated differential time-of-flight data set, such as a data set determined in a previous scan and stored for future retrieval.

As shown in FIG. 3, block S250 recites generating an acoustic speed rendering of the volume of tissue at least partially based on the difference between the observed differential time-of-flight data set and the calculated differential time-of-flight data set (double difference time-of-flight). Block S250 preferably functions to visually present the characteristics of the tissue based on the received acoustic.

As shown in FIG. 5, in a variation of the method of the preferred embodiment, the method further includes performing forward modeling in block S260, performing inverse modeling in block S270, iteratively repeating forward modeling and inverse modeling until convergence is met with a final acoustic speed model in block S280, and generating an acoustic speed rendering from the final acoustic speed model in block S290. Preferably, blocks S260, S270, and S280 collectively function to iteratively solve any nonlinear inversion problem resulting from bent-ray tomography, preferably by incorporating the calculation of the "double difference" term between physically adjacent waveforms. Ray paths of the acoustic waveforms (the orthogonal trajectories of the wavefronts) can be bent and/or distorted during transmission through tissue because the acoustic speed distribution of the tissue is not uniform. The forward modeling and inverse modeling preferably update the ray paths during each iteration to more accurately incorporate the ray bending effects.

Block S260 recites performing forward modeling and preferably functions to generate a calculated differential ToF data set for adjacent emitter-receiver pairs. In some variations of the method, a first iteration of blocks S260, S270, and S280 may additionally or alternatively incorporate an initial calculated differential time-of-flight data set from block S255. The ultrasound wave from a transmitter i arriving at receiver k at time T can be expressed using ray theory as a path integral $$T_k^i = \int_i^k u\, ds \tag{1}$$

where u is slowness (the inverse of acoustic speed) and ds is an element of ray path length. Forward modeling preferably solves the 2-D eikonal equation $$(\nabla E)^2 = (\partial T/\partial x)^2 + (\partial T/\partial y)^2 = (1/v)^2 = (s_x^2 + s_y^2) \tag{2}$$

where the (x, y) are discrete spatial grid coordinates, T is the travel time, v is the sound speed of waveforms in the acoustic coupling medium (e.g., water in the imaging tank), and $(s_x, s_y)$ is the slowness vector of the ultrasound wave. In the eikonal equation (2), E is a constant that describes the wavefronts. The ray paths are preferably traced using the slowness vector $(s_x, s_y)$ that can be obtained by calculating the gradient of the travel-time field. Forward modeling preferably includes solving the eikonal equation (2) using a grid travel-time tracing technique (which is known and readily understood by one skilled in the art), any other suitable finite-difference method, or any suitable eikonal solver. In forward modeling, the slowness field of the model (the first iteration may use an initial model, such as a homogeneous initial model) is preferably discretized in a uniform grid with equal-sized grid cells (e.g., rectangular cells).

As shown in FIG. 5, block S270 recites performing inverse modeling and preferably functions to generate an acoustic speed model based on the observed differential ToF data set and the calculated differential ToF data set. In some variations of the method, the generated acoustic speed model may supersede and/or supplement an initial acoustic speed model used in block S255. In inverse modeling, $\Delta t_i$ represents the difference between the ith picked ToF observed from the recorded ultrasound data and the ith calculated ToF calculated from the current forward acoustic speed model, such that $$\Delta t_i = t_i^{obs} - t_i^{cal} \quad (3)$$

The traditional inverse problem can be described as $$\sum_{j}^{M} l_{ij} \Delta s_j = \Delta t_i \quad (4)$$

where $\Delta s_j$ is the slowness perturbation for the jth grid cell, which needs to be inverted, and $l_{ij}$ is the ray length of the ith ray within the jth cell. Equation (4) can also be expressed in matrix form as $$L\Delta S = \Delta T \quad (5)$$

The subtraction of a similar equation respectively for an adjacent ray k from equation (4) results in the expression $$\Delta t_i - \Delta t_k = \sum_{j}^{M} l_{ij} \Delta s_j - \sum_{j}^{M} l_{kj} \Delta s_j \quad (6)$$

where $\Delta t_i - \Delta t_k$ is equivalent to the "double difference" term. The "double difference" term describes the difference between the observed and calculated differential ToFs for two physically adjacent rays, and can also be written as $$\Delta t_i - \Delta t_k = (t_i^{obs} - t_k^{obs}) - (t_i^{cal} - t_k^{cal}) \quad (7)$$

The observed differential ToFs $(t_i^{obs} - t_k^{obs})$ is preferably calculated during cross-correlation of the waveforms, but may alternatively be determined in any suitable manner. Equation (6) may also be expressed in matrix form as $$DL\Delta S = D\Delta T \quad (8)$$

where D, the differential operator matrix, has the form of $$D = \begin{bmatrix} 1 & -1 & \cdots & \cdots & \cdots & \cdots \\ 1 & \cdots & \cdots & -1 & \cdots & \vdots \\ \vdots & \cdots & \cdots & \cdots & \cdots & \vdots \\ \vdots & \cdots & 1 & \cdots & -1 & \vdots \\ \cdots & \cdots & \cdots & \cdots & \cdots & \cdots \end{bmatrix} \quad (9)$$

If A=DL is assumed to be the new kernel matrix and $\Delta TT = D\Delta T$ is the new data for the double difference inversion problem, equation (9) becomes $$A\Delta S = \Delta TT \quad (10)$$

As shown in FIG. 5, block S280 recites iteratively repeating forward modeling and inverse modeling until convergence in met with a final acoustic speed model. Block S280 preferably functions to derive a final acoustic speed model that is deemed sufficiently accurate.

Figure 6:
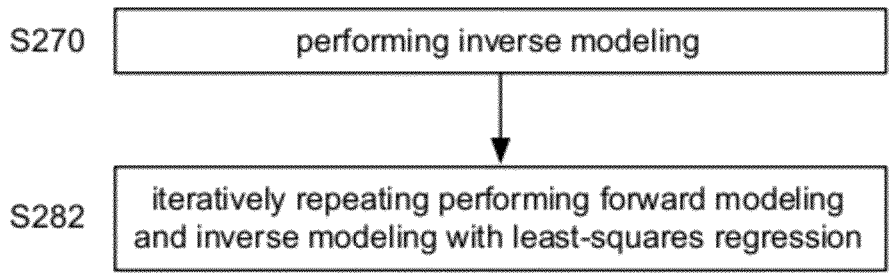

As shown in FIG. 6, in another variation of the preferred embodiment, the method includes block S282, which recites iteratively repeating performing forward modeling and inverse modeling with least-squares regression. Block S282 can be preferably performed until the residual between the observed differential ToF data set and the calculated differential ToF data set satisfies a desired (minimally acceptable) threshold, or generally until the difference between the observed and calculated differential ToF data sets is not further reduced from a previous iteration (or at least not further reduced by a particular amount). However, any suitable convergence criterion or suitable combination of convergence criteria may be used to evaluate whether to continue iteratively repeating the forward and inverse modeling steps.

As shown in FIG. 3, block S250 recites generating an acoustic speed rendering from the final acoustic speed model. Block S250 preferably functions to translate the final acoustic speed model (e.g., quantitative parameters) into a visual form. The resulting acoustic speed rendering, which incorporates the double difference term, is more accurate with higher precision and higher resolution than those derived using standard ultrasound ray tomography methods. The acoustic speed rendering generated in block S250 is more easily interpretable for screening, diagnosis, and/or any suitable application. The acoustic speed rendering may include two-dimensional "slices" of the tissue corresponding to respective cross-sections of the volume of tissue (e.g., image slices of discrete anterior-posterior positions of breast tissue), and/or a three-dimensional rendering resulting from a composite of multiple two-dimensional cross-sectional images, or alternatively resulting from scanning the volume of tissue in a three-dimensional manner. In some applications, the acoustic speed rendering may be combined and/or compared with additional renderings of the volume of tissue (e.g., attenuation, reflection).

The system and methods of the preferred embodiment can be embodied and/or implemented at least in part as a machine configured to receive a computer-readable medium storing computer-readable instructions. The instructions are preferably executed by computer-executable components preferably integrated with the system and one or more portions of the processor 140 and/or the controller 150. The computer-readable medium can be stored on any suitable computer readable media such as RAMs, ROMs, flash memory, EEPROMs, optical devices (CD or DVD), hard drives, floppy drives, or any suitable device. The computer-executable component is preferably a general or application specific processor but any suitable dedicated hardware device or hardware/firmware combination device can (alternatively or additionally) execute the instructions.

Example Implementations of the Preferred System and Method

The following example implementations of the preferred system and method are for illustrative purposes only, and should not be construed as definitive of limiting of the scope of the claimed invention. In a first example, a breast phantom was scanned using a toroidal ring transducer. The breast phantom provides tissue-equivalent scanning characteristics of highly scattering, predominantly parenchymal breast tissue. An X-ray CT scan of the breast phantom was also taken after the manufacture of the breast phantom (FIG. 7C) to benchmark its anatomical structure. The methods of double difference (DD) tomography and of standard tomography were applied to the acquired data of the breast phantom. A comparison of the DD tomography result with standard tomography is shown in FIGS. 7A, 7B, 7C, in which the sound speed scale is from 1470 m/s to 1550 m/s. Structures in both the DD tomogram (FIG. 7A) and the standard tomogram (FIG. 7B) are generally consistent with the X-ray CT image (FIG. 7C). The ultrasound scanning position was not exactly matching the position in FIG. 7C, which partially explains the size mismatch of the inclusions between FIGS. 7A-7C.

Figures 7, 8:
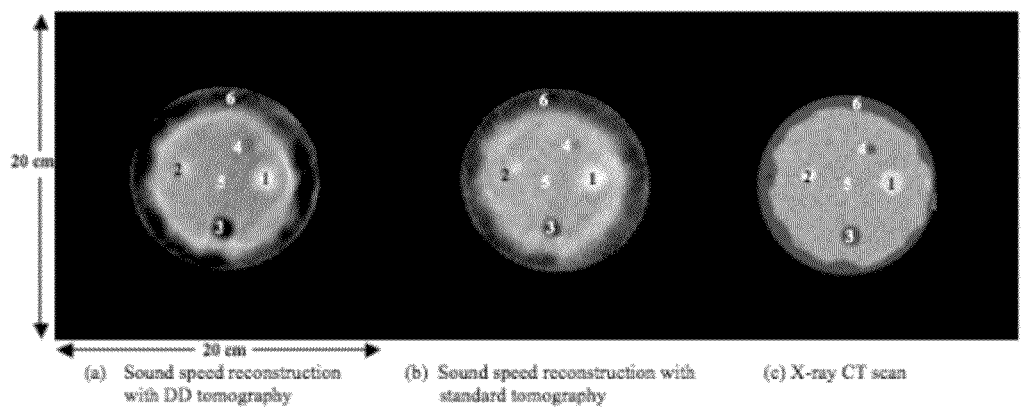
FIGS. 7-10 are examples of double different tomograms created using the method of a preferred embodiment, compared to other tomograms created using conventional methods.

Visual comparison of FIGS. 7A and 7B shows that the DD tomogram demonstrates better resolution and sharper image as well as less random noise. The images may be further assessed quantitatively by comparing the calculated sound speeds with known sound speeds obtained during manufacture. As shown in FIG. 8, the calculated sound speeds in the DD tomogram are more consistent with the known values, while sound speeds from standard tomography show larger discrepancies from known values.

Figure 9:
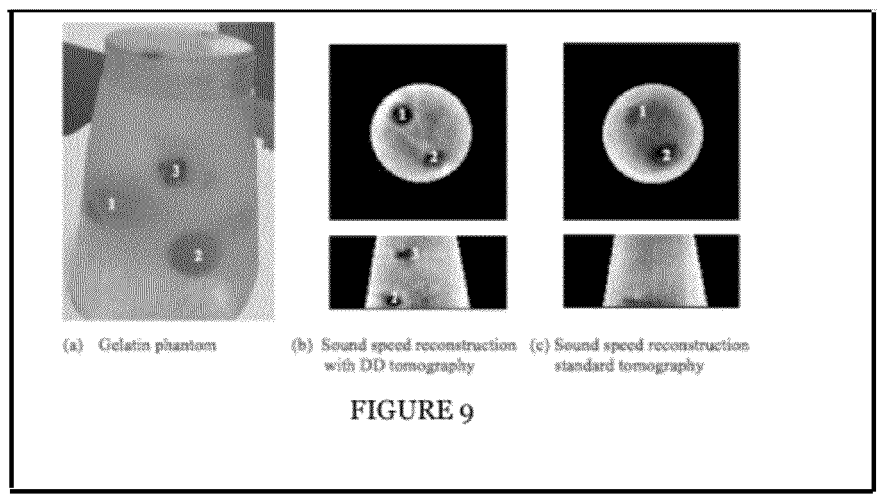

In a second example, a gelatin phantom (FIG. 9A) was prepared using plain gelatin powder with two embedded cherry tomatoes and one soft candy simulating rounded and irregular shaped inclusions. The phantom was scanned with a toroidal transducer array from top to bottom for a total of 40 slices to acquire acoustic data. The methods of DD tomography and of standard tomography were applied to the acquired data of the gelatin phantom. FIGS. 9B and 9C present examples of sound speed images for selected slices. DD tomography generally gives sharper images when compared to standard tomography. In the resliced cross-sections, DD tomography (FIG. 9B) successfully reconstructs the irregular shaped soft candy (marked as 3) and the rounded tomato (marked as 2) that are indiscernible in the corresponding standard tomogram (FIG. 9C). The resliced tomograms show that, compared to standard tomography, DD tomography has higher out-of-plane resolution, which is generally lower than in-plane resolution due to the nature of the toroidal array.

Figure 10:
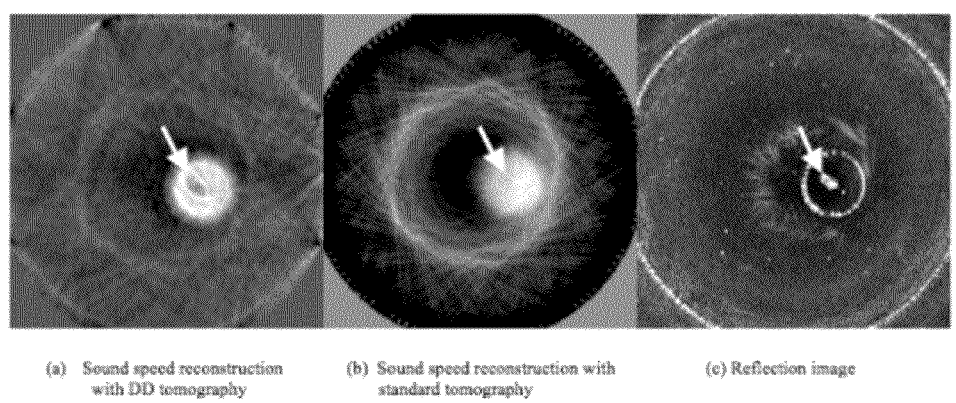

In a third example, six excised mouse mammary glands were scanned using a toroidal ring transducer. In order to minimize the movements during the scan, the mammary glands were soaked in a mixture of alcohol and saline in a latex container. The density of the fluid mixture was similar to the mammary glands under interrogation so that the mammary glands could stay steadily in the middle of the container for a stable scan. The methods of DD tomography and of standard tomography were applied to the acquired acoustic data for the six mouse mammary glands. An example of a cross-sectional sound speed image from DD tomography for one mouse mammary gland is shown in FIG. 10A, and may be compared to an analogous cross-sectional sound speed image from standard tomography shown in FIG. 10B. The corresponding reflection image is presented in FIG. 10C for better comparison. The mammary gland in FIG. 10C (indicated by arrow) shows as low sound speed in the DD tomogram (FIG. 10A), while it is not detectable in the standard tomogram (FIG. 10B).

As a person skilled in the art of will recognize from the previous detailed description of the preferred system and method, modifications and changes can be made to the preferred embodiments of the invention without departing from the scope of this invention defined in the following claims.

What is claimed is:

1. A system for imaging a volume of tissue, comprising:
an array of ultrasound emitters configured to surround the volume of tissue and emit acoustic waveforms toward the volume of tissue;
an array of ultrasound receivers configured to surround the volume of tissue and to receive a set of acoustic waveforms scattered by the volume of tissue, each acoustic waveform in the set of acoustic waveforms corresponding to a respective ultrasound emitter-ultrasound receiver pair, wherein the array of ultrasound emitters and the array of ultrasound receivers are arranged in a circular ring transducer configured to receive and encircle the volume of tissue;
a processor comprising a computer:
configured to determine a measured differential time-of-flight data set, at the computer, based on relative measured time-of-flights of adjacent acoustic waveforms, in the set of acoustic waveforms, corresponding to adjacent ultrasound emitter-ultrasound receiver pairs;
configured to determine a calculated differential time-of-flight data set according to a forward modeling algorithm, implementing theory, implementing ray theory, that processes the set of acoustic waveforms;
configured to determine a difference between the measured differential time-of-flight data set and the calculated differential time-of-flight data set between a first acoustic waveform and a second acoustic waveform, adjacent to the first acoustic waveform, of the set of acoustic waveforms; and
configured to generate an acoustic speed rendering of the volume of tissue based on the difference between the observed differential time-of-flight data set and the calculated differential time-of-flight data set; and
a display, in communication with the computer, configured to render the acoustic speed rendering to a user analyzing the volume of tissue.

2. The system of claim 1, wherein in determining the measured differential time-of-flight data set, the processor is configured to cross-correlate adjacent acoustic waveforms, of the set of acoustic waveforms, that are at least one of: a) originating from a common ultrasound emitter source and b) received at a common ultrasound receiver location.

3. The system of claim 1, wherein each ultrasound emitter is surrounded by at least two other ultrasound emitters.

4. The system of claim 3, wherein each ultrasound receiver is surrounded by at least two other ultrasound receivers.

5. The system of claim 4, wherein the array of ultrasound emitters and the array of ultrasound receivers are contiguously arranged in an axially symmetrical arrangement about a center point of the array of ultrasound emitters and the array of ultrasound receivers.

6. The system of claim 1, wherein in generating an acoustic speed rendering of the volume of tissue, the processor:
is configured to perform the forward modeling algorithm to generate the calculated differential time-of-flight data set for adjacent emitter-receiver pairs;
is configured to perform an inverse modeling algorithm to generate an acoustic speed model based on the measured differential time-of-flight data set and the calculated differential time-of-flight data set;
is configured to iteratively repeat the forward modeling algorithm and the inverse modeling algorithm until convergence is met with a final acoustic speed model; and
is configured to generate the acoustic speed rendering from the final acoustic speed model.

7. The system of claim 6, wherein in performing the inverse modeling algorithm, the processor is configured to implement a double difference term associated with two adjacent acoustic waveforms, of the set of acoustic waveforms, defined as the difference between a first differential time of flight for a subset of two adjacent acoustic waveforms of the measured differential time-of-flight data set and a second differential time of flight for the subset of two adjacent acoustic waveforms of the calculated differential time-of-flight data set.

8. The system of claim 7, wherein in iteratively repeating performing the forward modeling algorithm and the inverse modeling algorithm, the processor is configured to perform a least-squares regression.

9. The system of claim 8, wherein the processor is further configured to stop iteratively repeating performing the forward modeling algorithm and the inverse modeling algorithm when a residual criterion associated with the measured differential time-of-flight data set and the calculated differential time-of-flight data set meets a predetermined threshold.

10. A method for imaging a volume of tissue, comprising:
at a computer processor, receiving data representative of a set of acoustic waveforms originating from an array of ultrasound emitters surrounding the volume of tissue, scattered by the volume of tissue, and received with an array of ultrasound receivers surrounding the volume of tissue, wherein each acoustic waveform of the set of acoustic waveforms corresponds to a respective ultrasound emitter-ultrasound receiver pair;
at the computer processor determining a measured differential time-of-flight data set based on relative measured time-of-flights of adjacent acoustic waveforms, of the set of acoustic waveforms, corresponding to adjacent ultrasound emitter-ultrasound receiver pairs;
at the computer processor, determining a calculated differential time-of-flight data set according to a forward modeling algorithm, implementing ray theory, that processes the set of acoustic waveforms;
at the computer processor, determining a difference between the measured differential time-of-flight data set and the calculated differential time-of-flight data set between a first acoustic waveform and a second acoustic waveform, of the set of acoustic waveforms, adjacent to the first acoustic waveform;
at the computer processor, generating an acoustic speed rendering of the volume of tissue at least partially based on the difference between the observed differential time-of-flight data set and the calculated differential time-of-flight data set; and
at a display in communication with the computer processor, rendering the acoustic speed rendering to a user analyzing the volume of tissue.

11. The method of claim 10, further comprising emitting acoustic waveforms from an array of ultrasound emitters in which each ultrasound emitter is surrounded by at least two other ultrasound emitters.

12. The method of claim 10, further comprising receiving acoustic waveforms with an array in which each ultrasound receiver is surrounded by at least two other ultrasound receivers.

13. The method of claim 10, wherein determining the measured differential time-of-flight data set comprises cross-correlating adjacent acoustic waveforms, of the set of acoustic waveforms, that are at least one of: a) originating from a common ultrasound emitter source and b) received at a common ultrasound receiver location.

14. The method of claim 10, wherein generating the acoustic speed rendering of the volume of tissue includes:
performing the forward modeling algorithm to generate a calculated differential time-of-flight data set for the adjacent ultrasound emitter-ultrasound receiver pairs;
performing an inverse modeling algorithm to generate an acoustic speed model based on the measured differential time-of-flight data set and the calculated differential time-of-flight data set;
iteratively repeating the forward modeling algorithm and the inverse modeling algorithm until convergence is met with a final acoustic speed model; and
generating the acoustic speed rendering from the final acoustic speed model.

15. The method of claim 14, wherein performing the inverse modeling algorithm comprises implementing a double difference term associated with two adjacent acoustic waveforms, of the set of acoustic waveforms, defined as the difference between a first differential time of flight for a subset of two adjacent acoustic waveforms of the observed differential time-of-flight data set and a second differential time of flight for the subset of two adjacent acoustic waveforms of the calculated differential time-of-flight data set.

16. The method of claim 15, wherein iteratively repeating performing the forward modeling algorithm and the inverse modeling algorithm is performed with least-squares regression.

17. The method of claim 16, wherein iteratively repeating performing the forward modeling algorithm and the inverse modeling algorithm is stopped when a residual criterion associated with the observed differential time-of-flight data set and the calculated differential time-of-flight data set meets a predetermined threshold.

18. A method for imaging a volume of tissue, comprising:
at a computer processor, receiving data representative of a set of acoustic waveforms originating from an array of ultrasound emitters surrounding the volume of tissue, scattered by the volume of tissue, and received with an array of ultrasound receivers surrounding the volume of tissue, wherein each acoustic waveform of the set of acoustic waveforms corresponds to a respective ultrasound emitter-ultrasound receiver pair;
at the computer processor, determining a measured differential time-of-flight data set based on relative measured time-of-flights of adjacent acoustic waveforms, of the set of acoustic waveforms, corresponding to adjacent ultrasound emitter-ultrasound receiver pairs;
at the computer processor, generating a calculated differential time-of-flight data set for adjacent ultrasound emitter-ultrasound receiver pairs, according to a forward modeling algorithm, implementing ray theory;
at the computer processor, generating an acoustic speed model according to an inverse modeling algorithm applied to the measured differential time-of-flight data set and the calculated differential time-of-flight data set;
at the computer processor, iteratively repeating the forward modeling algorithm and the inverse modeling algorithm until convergence is met with a final acoustic speed model descending from the acoustic speed model; and
at a display in communication with the computer processor, rendering an acoustic speed image derived from the final acoustic speed model.

19. The method of claim 18, wherein receiving data representative of the set of acoustic waveforms comprises receiving data derived from the array of ultrasound emitters the array of ultrasound receivers, wherein the array of ultrasound emitters and the array of ultrasound receivers are arranged in a circular ring transducer configured to receive and encircle the volume of tissue.

* * * * *

UNITED STATES PATENT AND TRADEMARK OFFICE
CERTIFICATE OF CORRECTION

| | | |
|---|---|---|
| PATENT NO. | : 9,113,835 B2 | Page 1 of 1 |
| APPLICATION NO. | : 13/368169 | |
| DATED | : August 25, 2015 | |
| INVENTOR(S) | : Cuiping Li | |

It is certified that error appears in the above-identified patent and that said Letters Patent is hereby corrected as shown below:

In the Specification

In Column 1, Line 14, insert following header and paragraph:
--STATEMENT AS TO FEDERALLY SPONSORED RESEARCH
This invention was made with Government support under Grant R44CA165320 awarded by the National Institutes of Health (NIH) through the National Cancer Institute. The Government has certain rights in the invention.--

Signed and Sealed this
Sixth Day of August, 2024

Katherine Kelly Vidal
*Director of the United States Patent and Trademark Office*